(12) United States Patent
Erb

(10) Patent No.: US 7,438,726 B2
(45) Date of Patent: Oct. 21, 2008

(54) BALL HAND PROSTHESIS

(76) Inventor: Robert A. Erb, 230 Jug Hollow Rd., P.O. Box 86, Valley Forge, PA (US) 19481-0086

( * ) Notice: Subject to any disclaimer, the term of this patent is extended or adjusted under 35 U.S.C. 154(b) by 653 days.

(21) Appl. No.: 10/850,254

(22) Filed: May 20, 2004

(65) Prior Publication Data
US 2005/0261784 A1 Nov. 24, 2005

(51) Int. Cl.
A61F 2/66 (2006.01)
(52) U.S. Cl. .......................... 623/57; 623/65
(58) Field of Classification Search .................. 623/57, 623/61–65
See application file for complete search history.

(56) References Cited

U.S. PATENT DOCUMENTS

| 1,438,114 | A |   | 12/1922 | Hume            |        |
|-----------|---|---|---------|-----------------|--------|
| 2,657,394 | A | * | 11/1953 | Milton, Jr. et al. | 623/57 |
| 4,386,448 | A |   | 6/1983  | Kohn            | 16/121 |
| 4,735,754 | A | * | 4/1988  | Buckner         | 264/40.1 |
| 4,944,766 | A |   | 7/1990  | Williams        | 623/65 |
| 5,080,681 | A |   | 1/1992  | Erb             | 623/63 |
| 6,238,358 | B1 | * | 5/2001 | Philot et al.   | 602/5  |

OTHER PUBLICATIONS

Dechev et al, Multiple finger, passive adaptive grasp prosthetic hand, Oct. 2001, Mechanism and Machine Theory, vol. 36, issue 10, pp. 1157-1173.*
Dechev et al, Multi-finger, passive adaptive grasp prosthetic hand: Better function and Cosmesis, date unknown, pp. 1-2.*

* cited by examiner

Primary Examiner—William H. Matthews

(57) ABSTRACT

A realistic looking hand prosthesis made preferably of an elastomeric material is formed to hold a substantially spherical ball. The ball is held in the hand securely by friction between a ball and a hand made of a rubber like material wherein the ball is slightly larger in diameter than the conformed hand. The ball may be selectively rotationally oriented in three orthogonal directions of angular freedom. The ball is provided with various attachment means for attaching implements, which attachment means may include holes of various shapes and sizes, holes with projections, magnetic attaching means and threaded or other fastening means. Providing of angular adjustment in three orthogonal directions enables the ball to be able to attach a large number of useable implements to be positioned so as to aim the axis of each implement as needed and to rotate about its axis. The ball may be utilized in connection with a natural or prosthetic hand.

17 Claims, 4 Drawing Sheets

US 7,438,726 B2

BALL HAND PROSTHESIS

FIELD OF THE INVENTION

The present invention relates to a ball hand prosthesis. More particularly, the present invention relates to a ball hand prosthesis which is both functional and provides a highly realistic, natural appearance.

BACKGROUND OF THE INVENTION

There is a need for a prosthetic hand which is both functional and which provides a realistic natural appearance which can be very important for the social rehabilitation of amputees.

In the past, it has been possible to provide passive prosthetic hands which can provide some degree of realistic appearance, but without function. Alternatively, there are some prosthetic hands which provide some degree of function, such as hook devices and lobster/claw like graspers, but do not provide a realistic natural appearance of a hand nor do they provide the versatility and effectiveness of function provided by the present invention.

SUMMARY OF THE INVENTION

The present invention provides a very realistic appearance and the ability to hold a variety of objects, while providing light weight, durability and low cost.

The present invention provides a highly realistic appearance.

The present invention provides the ability to hold various objects.

The present invention provides a lightweight prosthesis, ease of use, durability, low maintenance and low cost.

The present invention comprises a hand member which is conformed to hold a substantially spherical ball. The ball is provided with a plurality of means for selectively attaching various implements. In the present invention, the ball holds the implements, not the prosthetic hand directly.

In accordance with the present invention, the ball within the conformed aesthetically pleasing hand is provided with rotational movement such that it can be oriented in three orthogonal directions of angular freedom. The providing of angular adjustment in three orthogonal directions enables the ball to be able to attach a large number of useable implements to be positioned so as to aim the axis of each implement as needed and to rotate about that axis. For example, not only can a spoon be held by the appropriate attachment of the ball, but the axis of the spoon and the rotary position of the spoon can be set such that the spoon can be used effectively for feeding.

In accordance with the present invention, a high coefficient of friction is provided between the ball and the prosthetic hand to allow the determined orientation to be maintained as long as it is needed. In addition to the high coefficient of friction, the orientation of the ball is maintained by the spring action of the elastomeric fingers of the hand around a ball having a diameter which is slightly larger than the diameter of the hand shape when the elastomeric fingers are in their natural position. In other words, a sphere is used for making a particular donor mold which has a diameter slightly smaller than that of the ball to be used with the prosthetic hand to be derived from that mold.

Briefly and basically, in accordance with the present invention, a hand prosthesis is provided which comprises a hand member which is formed to hold a substantially spherical ball member and the substantially spherical ball member is adapted to be retained within the hand member, with the ball including means for attaching a tool, object or other implement. The present invention is also directed to the apparatus itself for holding the implements which includes a substantially spherical shaped ball adapted to be held in a natural or prosthetic hand with the ball being provided with means for selectively attaching a plurality of implements and whereby the ball can be positioned within the hand such that it can be rotationally oriented in three orthogonal directions of angular freedom.

BRIEF DESCRIPTION OF THE DRAWINGS

For the purpose of illustrating the invention, there are shown in the drawings forms which are presently preferred; it being understood, however, that this invention is not limited to the precise arrangements and instrumentalities shown.

DETAILED DESCRIPTION OF THE PREFERRED EMBODIMENTS

Figure 1:
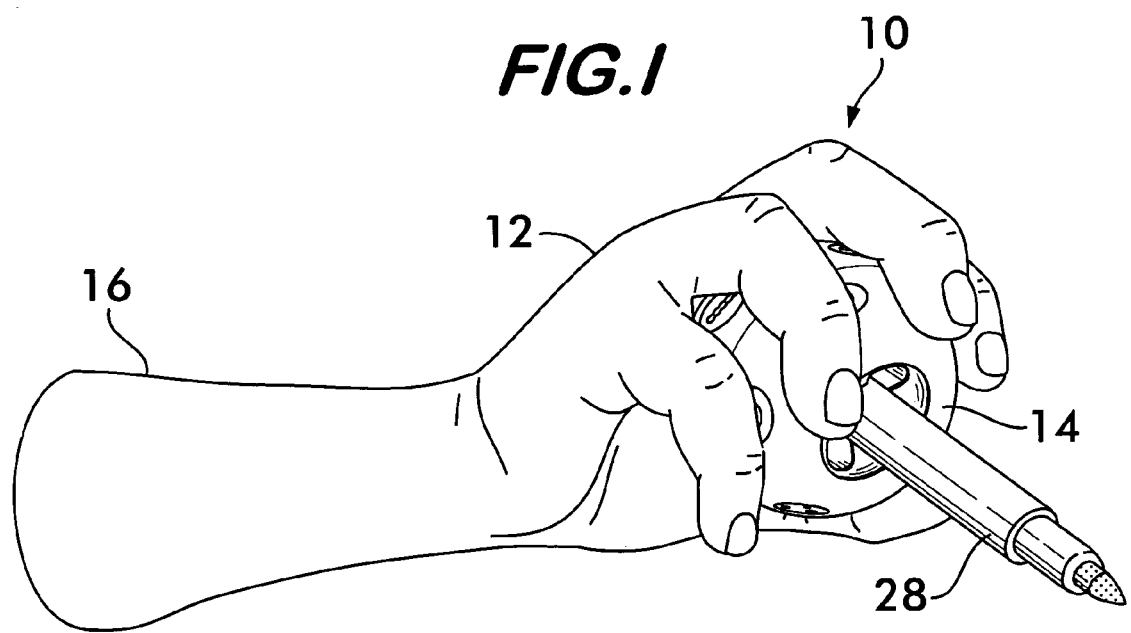
FIG. 1 is a view in perspective of a ball hand prosthesis holding a implement in accordance with the present invention.

Referring now to the drawings, wherein like numerals indicate like elements, there is shown in FIG. 1 a ball hand prosthesis 10 comprised of a hand or a hand member 12 and a ball or ball member 14. Hand or hand member 12 is further illustrated in FIG. 2. Ball or ball member 14 is further illustrated in FIGS. 3, 4 and 5.

Figure 2:
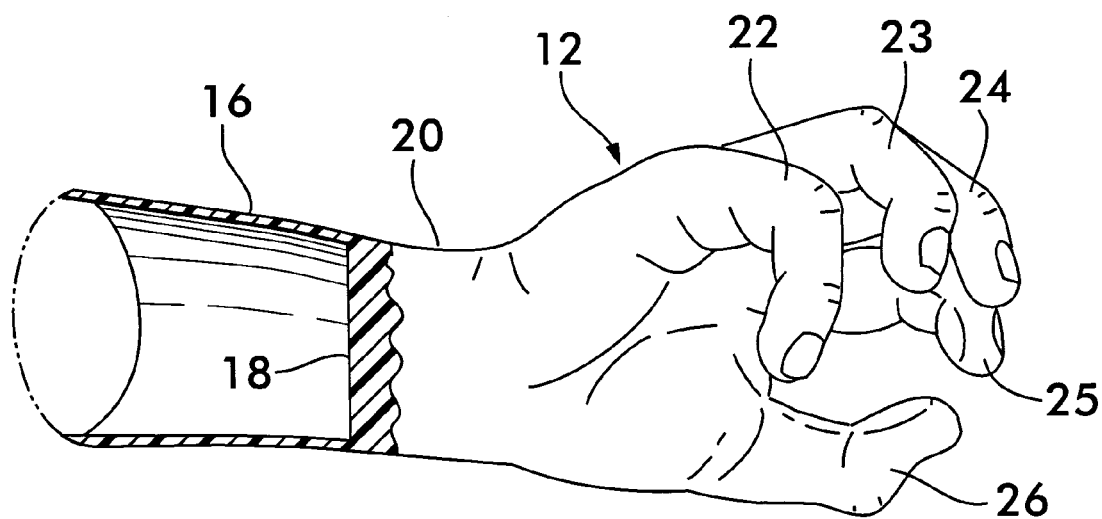
FIG. 2 is a view in perspective, partially broken away, of the hand portion of the prosthesis illustrated in FIG. 1.

Referring now to FIGS. 1 and 2, hand 12 is preferably constructed of an elastomeric material such as silicone rubber. However, other suitable elastomeric materials may be utilized and some examples of such suitable materials are given hereinafter. Hand 12 is constructed such that it provides a realistic appearance of a hand. Hand 12 may be colored to portray realistic hand qualities including realistic hands, fingers and fingernails. The coloring may be done by means of extrinsic coloration (coloration on the surface) or preferably may be done by multilayer intrinsic coloration in which the hand is built up in layers with each layer being colored. Intrinsic coloration provides enhanced realistic effects in that the hand has some translucent qualities similar to that of a real hand of a person. Hand 12 may be formed with an external silicone surface which extends proximately to form a sleeve 16 from terminal area 18. Sleeve 16 extends proximately from terminal area 18 which may be positioned in the wrist region or arm region of the amputee depending upon where the amputation or other deformity has occurred. In other words, portion 20 of hand or hand member 12 may be longer or shorter to place hand 12 at the proper length from the elbow.

Hand or hand member 12 is formed to hold a substantially spherical member as illustrated in FIGS. 1 and 2. In other words, fingers or digits 22 through 26 (which includes the thumb) are formed or conformed to hold a substantially spherical ball member. In a presently preferred embodiment, digits 22 through 26 are formed of an elastomeric material such as silicone rubber to fit or receive a ball of a diameter slightly less than the diameter of ball 14. In this manner, digits 22 through 26 must be flexed outwardly slightly to hold ball 14 thereby placing additional pressure on ball 14, which in combination with the friction between hand 12 including digits 22 through 26 and ball 14, the ball may be securely positioned and held in a particular orientation as illustrated in FIG. 1.

Ball 14 is a substantially spherical ball, and in a presently preferred embodiment would be a spherical ball. Ball 14 as held in hand or hand member 12 can be rotationally oriented in three orthogonal directions of angular freedom. The providing of angular adjustment in three orthogonal directions enables the ball to be able to attach a large number of useable implements to be positioned so as to aim the axis of each implement as needed and to rotate about the axis of the implement. For example, not only can a spoon be held by the appropriate attachment of the ball, but the axis of the spoon and the rotary position of the spoon can be adjusted or set such that the spoon can be used effectively for feeding. The term implement as used herein means any and every type of tool, object or device which can be used for any purpose, including, but not limited to: eating utensils such as spoons, knives and forks; writing instruments such as pencils, pens, markers, crayons, chalk, paint brushes, etc.; personal care devices such as toothbrushes, lipsticks, fingernail files, combs and the like; and other useful items such as credit cards, cards, licenses, flashlights, coins, tickets, currency, paper items and the like. Further, an implement would include any type of a tool or device that may be connected by any suitable means including, but not limited to, threaded connections and magnetic connections. Further, an implement would include various useful items such as keyboard key pushers, hooks of various types including simple hooks, grappling hooks, hook and loop components, magnets, C-clamps and spring clamps.

In a presently preferred embodiment, the ball may be made of silicone rubber. However, the ball may be made of various rubber type materials including polyurethane rubber, ethylene-vinyl acetate copolymer, plasticized polyvinyl chloride and thermoplastic elastomer.

Figure 3:
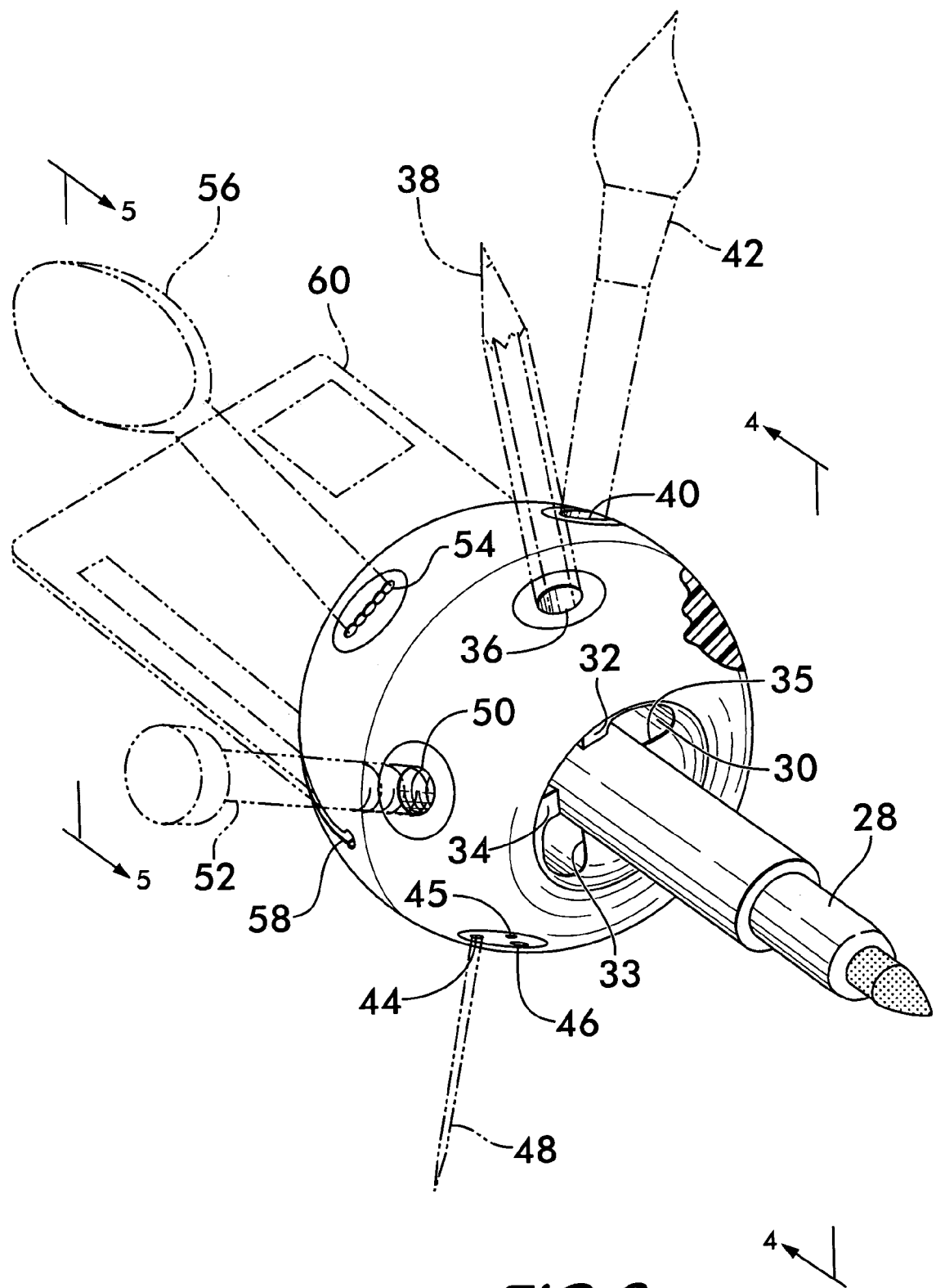
FIG. 3 is a view in perspective, partially broken away, of the ball portion of the prosthesis illustrating various implements attached thereto, some of them in dotted outline form.

Referring now to FIG. 3, there is shown a view in perspective of a ball member which includes a marker pen 28 held in a hole 30. Marker pen 28 is also shown in FIG. 1. Hole 30 is provided with projections 32, 33, 34 and 35 which may be compressed allowing hole 30 to receive items of various diameters. There is also shown in FIG. 3 in dotted outline form a hole 36 holding a pencil 38. There is also shown a hole 40 holding a paint brush 42. Holes 44, 45 and 46 are a plurality of holes of various small diameters which may be utilized to hold small objects. Toothpick 48 is shown retained in hole 44. It is understood that all of the implements shown in the drawings, and particularly in FIG. 3, are examples, and are not intended to be limiting. In other words, various implements other than marker 28, pencil 38, paintbrush 42 and toothpick 48 may be held in the various holes. There is also illustrated in FIG. 3 a threaded hole 50 which receives a threaded implement 52 such as a keyboard pusher. Also illustrated in FIG. 3 is a elongated hole or opening 54 with protruding projections for holding various implements. An implement in the form of a spoon 58 is illustrated in elongated hole 54. There is also provided a slot 58 for receiving implements in the form of planar members, such as cards, credit cards, keys and the like. The example illustrated in FIG. 3 is an implement in the form of credit card 60 in slot 58.

Figure 4:
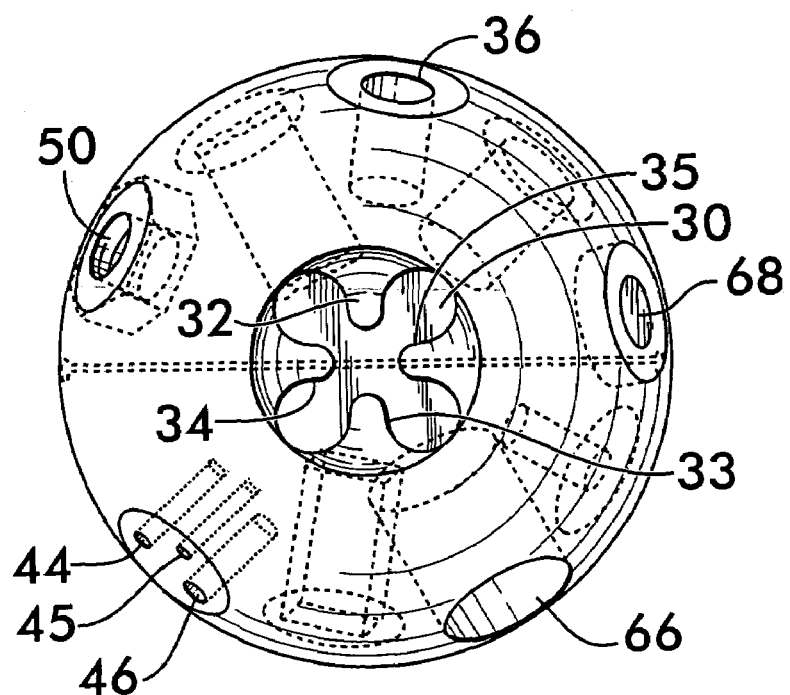
FIG. 4 is a view in elevation of one side of the ball portion of the prosthesis illustrating some of the implement attaching means in dotted outline form.

Referring now particularly to FIG. 4, there is shown another hole 66 of somewhat larger diameter for receiving an implement. There is also shown a hole 68 for receiving an implement.

Figure 5:
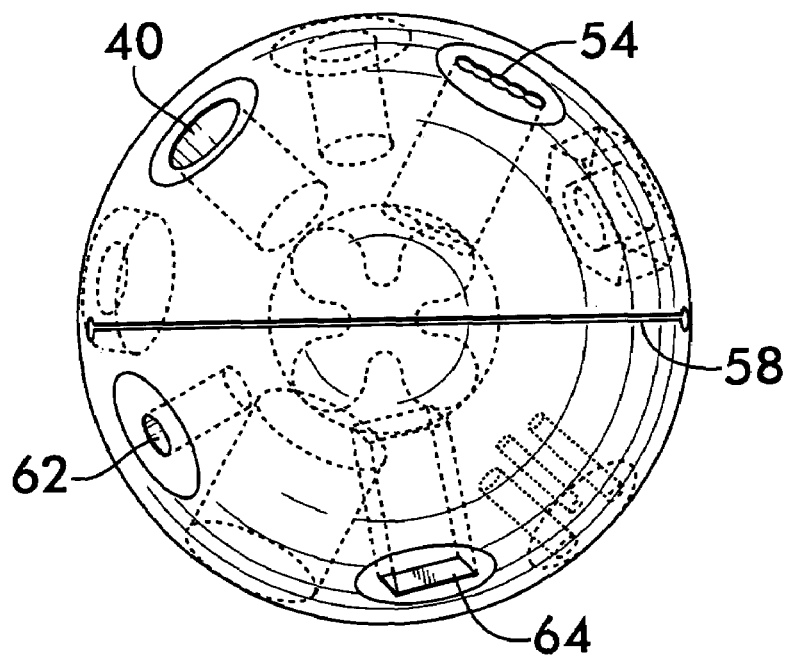
FIG. 5 is a view in elevation of the opposing side of the ball portion of the prosthesis, with some of the attaching means shown in dotted outline form.

Referring now to FIG. 5, there is shown a magnet 62 formed in ball 14 which functions as an attaching means. Also shown in FIG. 5 is a rectangular hole 64 which functions as an attaching means.

In constructing hand 10, hand 10 is preferably constructed of multiple layers of silicone rubber wherein each layer is provided with coloring, which preferentially produces a very realistic appearance of a natural hand. This would include appropriate coloration for the fingernails and appropriate coloration for the fleshy portions of the hand. The hand may preferably be constructed having a number of layers in the range of 3 to 13, but a smaller or larger number of layers may be utilized. Furthermore, it is understood that various other means of constructing hand 10 may be utilized including molding of a hand and providing a single layer of extrinsic coloration.

As indicated above, the hand is preferably constructed of multiple layers of silicone rubber. However, various other elastomeric materials may be utilized including polyurethane rubber, ethylene-vinyl acetate copolymer, plasticized polyvinyl chloride and thermoplastic elastomer. Other suitable elastomeric materials may be utilized in practicing the invention.

Ball 20 may be constructed of similar materials including preferably silicone rubber. However, other rubber-like materials may be used including polyurethane rubber, ethylene-vinyl acetate copolymer, plasticized polyvinyl chloride and thermoplastic elastomer. Other suitable materials may be utilized. In practicing the present invention, it is desirable to select materials for the hand and ball which have a high coefficient of friction between them. The high coefficient of friction along with the elastomeric fingers (five fingers including the thumb) formed to a diameter smaller than that of the diameter of ball 14 provides significant ability to retain the ball within the hand in any specific orientation while holding an implement with which functions may be performed.

In molding the ball, preferably the ball is molded in a split mold, each half of which has a substantially hemispherical inner surface. Each mold half has retractable form-element inserts which are positioned within the hemisphere to form the holes or openings which serve as the attachment means. The retractable form elements may be retracted from the mold prior to opening the mold and removing the molded ball.

Figure 6:
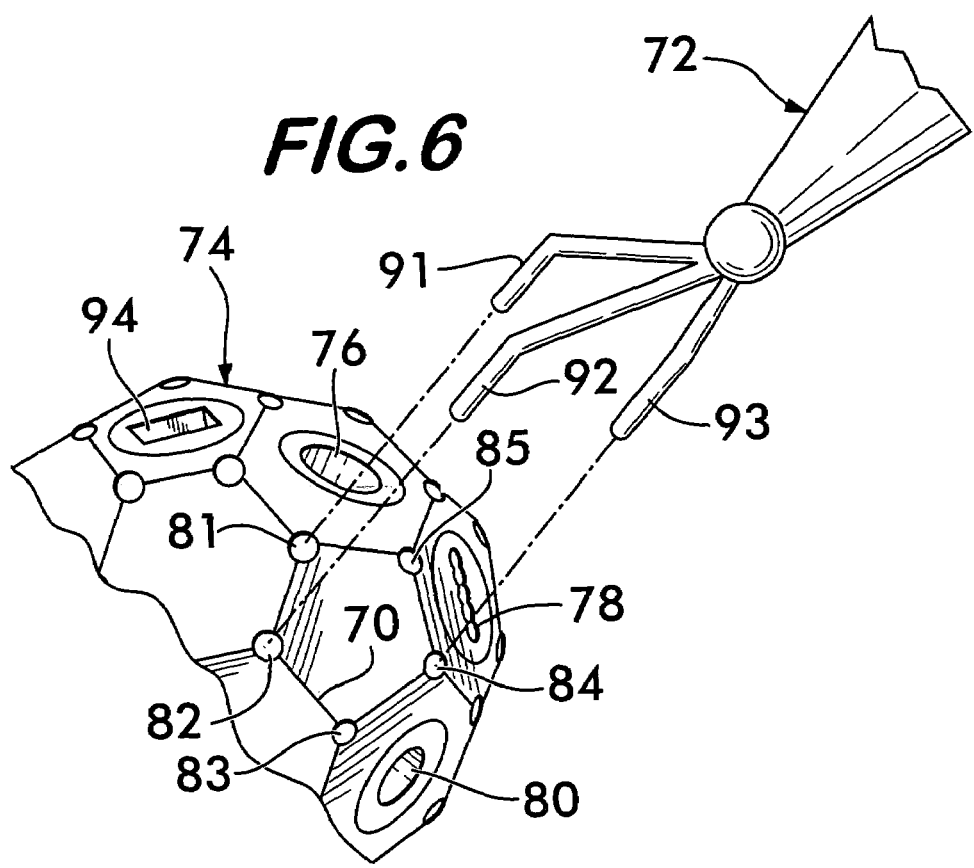
FIG. 6 is a view in perspective, partially broken away, of another embodiment of the ball portion of the prosthesis illustrating a polyhedral surface on the ball and another form of attaching means.

Referring now to FIG. 6, there is shown a view in perspective, partially broken away, of another embodiment of a ball 74 and an implement 72. Ball 74 is substantially spherical and illustrates one form of a polyhedral surface on the surface of ball 74. The polyhedral surface illustrated on ball 74 is that of a pentagon 70 with holes 81 through 85 located at each inward angle of the pentagon. A plurality of prongs on implement 72 may be arranged to mate with a plurality of holes functioning as a unit. For example, prongs 91, 92 and 93 may mate with holes 81, 82 and 83, respectively. One advantage of an implement 72 with a plurality of prongs mating with a plurality of holes functioning as a unit is that the implement is more firmly held to the ball and resists being pulled away from the ball 74. Also, any possibility of an implement rotating within a single hole is eliminated. In other words, implement 72 cannot rotate with respect to ball 74. As illustrated in FIG. 6, ball 74 may be provided with a plurality of holes or openings for receiving various implements similar to those described with respect to ball 14. For example, as illustrated in FIG. 6, there is a rectangular hole 94 as shown. There are also illustrated in FIG. 6 holes 76 and 80 as well as elongated hole 78 with inward projections.

Figure 7:
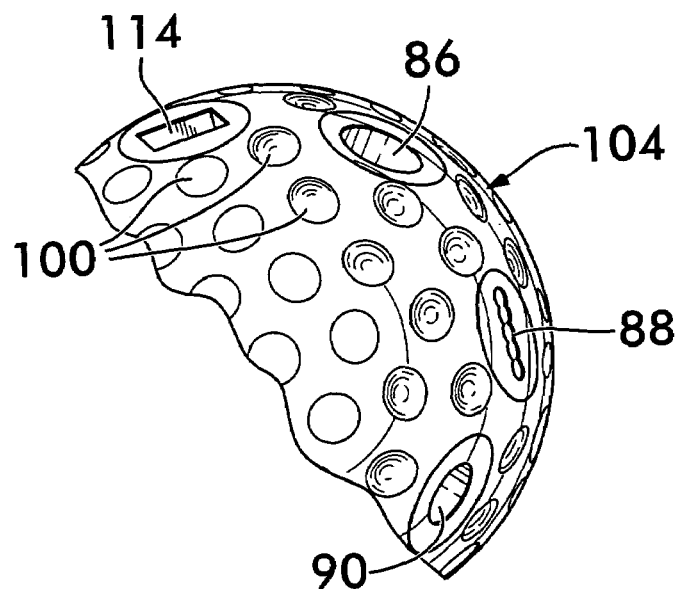
FIG. 7 is a view in perspective, partially broken away, of another embodiment of the ball portion of the prosthesis in accordance with the present invention illustrating a dimpled surface on the ball.

Referring now to FIG. 7, there is shown another embodiment of a substantially spherical ball 104 provided with dimples 100 on its surface. The dimpling provides a different surface texture and may be useful in handling and positioning of the orientation of the ball within the hand. Ball 104 may be provided with any and/or all of the attachment means as described with respect to ball 14. There is illustrated in FIG. 7 a rectangular hole or opening 114, round holes or openings 86 and 90 and elongated hole 88 provided with inward projections to enhance retention of an implement.

It will be appreciated to those skilled in the art that various modifications may be made to the present invention. Various surface contours may be used on the ball, even though it is substantially spherical. Further, slightly non-spherical shapes may be utilized for the ball, but preferably the ball is substantially spherical. Various forms of attachment or fastening means may be utilized to fasten implements to the ball.

In view of the above, the present invention may be embodied in other specific forms without departing from the spirit or essential attributes thereof and, accordingly, reference should be made to the appended claims, rather than to the foregoing specification as indicating the scope of the invention.

I claim:

1. A prosthetic combination comprising a substantially spherical ball member; a passive prosthetic hand member which is formed to hold and holds said substantially spherical ball member; said hand member being molded of an elastomeric material having digits molded in a curved shape with sufficient curvature to hold securely a sphere having a diameter less than, said substantially spherical ball member whereby said digits must be flexed outwardly to insert said substantially spherical ball member and said digits providing an inward force to hold substantially spherical ball member; and said substantially spherical ball member being forcibly retained within said hand member and including a plurality of different means for attaching an implement, wherein the plurality of different means are selected from the group consisting of a slot, a female threaded fitting, a hole, and a magnet.

2. A hand prosthesis in accordance with claim 1 wherein at least one of an inner surface of said hand member or an outer surface of said substantially spherical ball member is comprised of materials selected to provide friction between said hand member and said substantially spherical ball member.

3. A hand prosthesis in accordance with claim 1 in which said hand member is fabricated of silicone rubber.

4. A hand prosthesis in accordance with claim 3 in which the hand member is colored by means of multilayer intrinsic coloration.

5. A hand prosthesis in accordance with claim 1 in which the substantially spherical ball being held in the hand can be rotationally oriented in three orthogonal directions of angular freedom.

6. A hand prosthesis in accordance with claim 1 in which the substantially spherical ball member is made of material selected from the group consisting of silicone rubber, polyurethane rubber, ethylene-vinyl acetate copolymer, plasticized poly vinyl chloride and thermoplastic elastomer.

7. A hand prosthesis in accordance with claim 1 in which the substantially spherical ball member attaching means includes at least one slot.

8. A hand prosthesis in accordance with claim 1 in which the substantially spherical ball member attaching means includes at least one hole.

9. A hand prosthesis in accordance with claim 1 in which the substantially spherical ball member attaching means includes at least one female threaded fitting.

10. A hand prosthesis in accordance with claim 1 in which the substantially spherical ball member attaching means includes at least one magnet.

11. A hand prosthesis in accordance with claim 1 in which the substantially spherical ball member is adapted to hold items selected from the group consisting of: spoon, fork, knife, pencil, pen, marker, crayon, chalk, paintbrush, toothbrush, lipstick, key, fingernail file, comb, flashlight, card, coin, ticket, currency, paper item, and male threaded fitting.

12. A hand prosthesis in accordance with claim 1 in which the substantially spherical ball member is adapted to hold extension tools selected from the group consisting of: keyboard key pusher, simple hook, grappling hook, hook-and-loop component, magnet, C-clamp and spring clamp.

13. A hand prosthesis in accordance with claim 1 wherein said hand member is formed of elastomeric material.

14. A hand prosthesis in accordance with claim 13 wherein said elastomeric material is selected from the group consisting of silicone rubber, polyurethane rubber, ethylene-vinyl acetate copolymer, plasticized poly vinyl chloride and thermoplastic elastomer.

15. A hand prosthesis in accordance with claim 1 in which the substantially spherical ball member is a polyhedral surface.

16. A hand prosthesis in accordance with claim 1 in which the substantially spherical ball member has a dimpled surface.

17. A hand prosthesis in accordance with claim 1 wherein said substantially spherical ball member's means for attaching includes at least one attachment means comprised of a plurality of holes which mate with a tool or object having a plurality of prongs.

* * * * *